US012569617B2

(12) United States Patent
Tong et al.

(10) Patent No.: US 12,569,617 B2
(45) Date of Patent: Mar. 10, 2026

(54) INFUSION SET WITH ROTATABLE HUB AND PROCESS

(71) Applicant: Medtronic MiniMed, Inc., Northridge, CA (US)

(72) Inventors: Davy Tong, Thousand Oaks, CA (US); Hsi C. Fusselman, Simi Valley, CA (US); Kiem H. Dang, Thousand Oaks, CA (US); Sarnath Chattaraj, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 200 days.

(21) Appl. No.: 17/405,983

(22) Filed: Aug. 18, 2021

(65) Prior Publication Data

US 2023/0055871 A1     Feb. 23, 2023

(51) Int. Cl.
*A61M 5/162*          (2006.01)
*A61M 5/142*          (2006.01)
*A61M 5/158*          (2006.01)

(52) U.S. Cl.
CPC ........ *A61M 5/162* (2013.01); *A61M 5/14244* (2013.01); *A61M 2005/14284* (2013.01);
(Continued)

(58) Field of Classification Search
CPC .............. A61M 5/162; A61M 5/14244; A61M 2005/14284; A61M 2005/1586;
(Continued)

(56) References Cited

U.S. PATENT DOCUMENTS

| 3,993,208 A | 11/1976 | Ostrowsky |
| 5,865,330 A | 2/1999 | Buono |

(Continued)

FOREIGN PATENT DOCUMENTS

| WO | WO-99/44655 A2 | 9/1999 |
| WO | WO-2020/084374 A1 | 4/2020 |
| WO | WO-2020/097552 A1 | 5/2020 |

OTHER PUBLICATIONS

Extended European Search Report issued by by the European Patent Office on Dec. 13, 2022, 8 pages, for corresponding EP Application No. 22189642.6.

(Continued)

*Primary Examiner* — Kami A Bosworth
*Assistant Examiner* — Avery Smale
(74) *Attorney, Agent, or Firm* — Foley & Lardner LLP

(57) ABSTRACT

A hub member for an infusion set device includes a body and pads configured to receive a squeezing force directed radially inward relative to an axis of the body. The body compresses radially inward relative to the axis in response to the squeezing force. A plurality of connection features on the body are moveable from a first position radially inward toward a second position when the hub member is compressed radially inward. The plurality of connection features engage one or more further connection features on a housing to attach the hub member to the housing when the plurality of connection features are in the first position, and disengage the one or more further connection features to release the hub member when the plurality of connection features are moved toward the second position.

23 Claims, 13 Drawing Sheets

(52) U.S. Cl.
CPC ............... *A61M 2005/1586* (2013.01); *A61M 2005/1587* (2013.01); *A61M 2207/00* (2013.01)

(58) Field of Classification Search
CPC ...... A61M 2005/1587; A61M 2207/00; A61M 5/14248; A61M 2039/0288; A61M 39/10; A61M 39/1011; A61M 2039/1033; A61M 39/1055; A61M 2205/0216; A61M 2005/14252; A61M 2005/14268; A61M 5/158; A61M 39/0247; A61M 2039/0282; A61M 39/04; A61M 25/02; A61M 2025/028
See application file for complete search history.

(56) References Cited

U.S. PATENT DOCUMENTS

| | | | |
|---|---|---|---|
| 7,211,068 | B2 | 5/2007 | Douglas |
| 7,407,491 | B2 | 8/2008 | Fangrow, Jr. |
| 8,317,759 | B2 | 11/2012 | Moberg et al. |
| 8,956,330 | B2 | 2/2015 | Fangrow, Jr. |
| 10,105,484 | B2 | 10/2018 | Sonderegger et al. |
| 10,327,997 | B2 | 6/2019 | Griffith et al. |
| 10,682,462 | B2 | 6/2020 | Howell et al. |
| 2004/0204690 | A1 | 10/2004 | Yashiro et al. |
| 2007/0185441 | A1* | 8/2007 | Fangrow, Jr. ..... A61M 25/0612 604/93.01 |
| 2009/0163878 | A1* | 6/2009 | Moberg ................ A61M 25/02 604/263 |
| 2014/0088550 | A1* | 3/2014 | Bene .................... A61M 5/158 604/506 |
| 2018/0318550 | A1 | 11/2018 | Chiu et al. |
| 2020/0384187 | A1 | 12/2020 | Pham et al. |

OTHER PUBLICATIONS

Communication pursuant to Article 94(3) EPC, for corresponding EP Application No. 22189642.6, mailed Jun. 26, 2025, 8 pages.

* cited by examiner

INFUSION SET WITH ROTATABLE HUB AND PROCESS

BACKGROUND

The present disclosure relates, in general, to infusion sets or other medical devices with rotatable hubs.

Certain diseases or conditions may be treated, according to modern medical techniques, by delivering a medication or other substance to the body of a user, subcutaneously, through an infusion set, injection port or other medical device. For example, diabetes is commonly treated by delivering defined amounts of insulin to the user at appropriate times.

An infusion set can be used to facilitate frequent or continuous, subcutaneous infusion of a medication or other infusion media. Infusion sets as described herein include one or more cannula that can be inserted under the skin of the patient to deliver controlled amounts of infusion media to the patient. Such infusion sets may provide continuous delivery of infusion media from portable pumps carried with the patient, or from non-ambulatory pumps or devices in non-ambulatory environments. When used with a portable pump, the infusion set may be connected to the pump via a fluid line, such as a flexible medical tubing. Another application of an infusion set is to permit multiple injections of medication into a patient without the need to re-puncture the patient's skin. In that application, medication may be injected from a standard medical implement (such as, but not limited to a syringe), through an elastomer septum into the infusion set, for subcutaneous delivery from the infusion set.

Various examples of other infusions sets are described in U.S. Patent Application Publication No. 2018/0318550 (application Ser. No. 15/973,471 and U.S. Patent Application Publication No. 2020/0384187 (application Ser. No. 16/436, 496), each of which is incorporated herein by reference, in its entirety.

SUMMARY

An infusion set device according to certain examples described herein includes a housing having a first surface configured to be secured to a patient's skin and a hub member configured to engage and releasably attach to the housing. The hub member has a plurality of pads that are configured to receive a squeezing force directed radially inward relative to an axis of the hub member, wherein at least a portion of the hub member is configured to compress radially inward relative to the axis in response to the squeezing force being received by the pads. The infusion set device includes a plurality of connection features on the portion of the hub member, the plurality of connection features being moveable from a first position radially inward relative to the axis toward a second position when the portion of the hub member is compressed radially inward. The connection features are configured to engage one or more further connection features on the housing to attach the hub member to the housing when the connection features are in the first position. The connection features configured to disengage the one or more further connection features on the housing to release the hub member from being attached to the housing when the connection features are moved a definable distance toward the second position.

In certain further examples, the plurality of connection features on the hub member comprise a plurality of feet or protrusions extending radially outward relative to the axis.

In certain further examples, the connection features on the hub member and further connection features on the housing are configured to allow the hub member to be rotatable about the axis relative to the housing when the hub member is engaged with the housing and the connection features are moved the definable distance toward the second position, and are configured to inhibit the hub member from rotating about the axis relative to the housing when the hub member is engaged and attached with the housing and the connection features are in the first position.

In certain further examples, the connection features and further connection features are configured to allow the hub member to be rotatable about the axis relative to the housing when the hub member is engaged and attached with the housing and the connection features are in the first position.

In certain further examples, the hub member has a disc-shaped body that is coaxial with the axis, and wherein the plurality of pads comprise first and second pads located on opposite sides of the axis.

In certain further examples, the portion of the hub member that is configured to compress radially inward comprises at least a portion of the disc-shaped body made of a compressible material.

In certain further examples, the hub member further comprises a plurality of legs, where each leg has at least one of the connection features, and each leg extends outward from one side of the disc-shaped body.

In certain further examples, the plurality of connection features on the hub member comprise at least one foot or protrusion on each leg and extending radially outward relative to the axis.

In certain further examples, the hub member further comprises a cannula member having a fluid channel and configured to extend at least partially into a connection port on the housing when the hub member is engaged with the housing.

In certain further examples, the hub member has a body and the cannula of the hub member has a first length portion that extends from the body of the hub member and is received at least partially into the connection port of the housing when the hub member is engaged with the housing. In addition, the cannula of the hub member has a second length portion that flares or tapers outward to a wider outer diameter relative to the first length portion, the second length portion coupling the first length portion to the body of the hub member.

In certain further examples, the hub member further comprises a port for connection to a fluid flow conduit, the port being in fluid flow communication with the fluid channel of the cannula of the hub member.

Certain further examples relate to a hub member for an infusion set device, where the hub member includes a body and a plurality of pads that are configured to receive a squeezing force directed radially inward relative to an axis of the body, wherein at least a portion of the body is configured to compress radially inward relative to the axis in response to the squeezing force being received by the pads. The hub member further includes a plurality of connection features on the portion of the body, where the plurality of connection features are moveable from a first position radially inward relative to the axis toward a second position when the portion of the hub member is compressed radially inward. The connection features are configured to engage one or more further connection features on a housing to attach the hub member to the housing when the connection features are in the first position. The connection features are configured to disengage the one or more further connection features on the housing to release the hub member from being attached to the housing when the connection features are moved a definable distance toward the second position.

In certain further examples of the hub member, the plurality of connection features on the hub member comprise a plurality of feet or protrusions extending radially outward relative to the axis.

In certain further examples of the hub member, the body has a disc-like shape and the axis corresponds to the axis of the disc-like shape, and wherein the plurality of pads comprise first and second pads located on opposite sides of the axis.

In certain further examples of the hub member, the body further comprising a plurality of legs, each leg having at least one of the connection features, each leg extending outward from one side of the disc-like shaped body.

In certain further examples of the hub member, the plurality of connection features comprise at least one foot or protrusion on each leg and extending radially outward relative to the axis.

Certain further examples of the hub member include a cannula member having a fluid channel and configured to extend at least partially into a connection port on the housing when the hub member is engaged with the housing.

In certain further examples of the hub member, the cannula member has a first length portion that extends from the body of the hub member and is configured to be received at least partially into the connection port of the housing when the hub member is engaged with the housing. In addition, the cannula member has a second length portion that flares or tapers outward to a wider outer diameter relative to the first length portion. The second length portion coupling the first length portion to the body of the hub member.

Certain further examples relate to a method of making a hub member for an infusion set device, including providing a body, configuring a plurality of pads to receive a squeezing force directed radially inward relative to an axis of the body, and configuring at least a portion of the body to compress radially inward relative to the axis in response to the squeezing force being received by the pads. The method further includes connecting or forming a plurality of connection features on the portion of the body, to be moveable from a first position radially inward relative to the axis toward a second position when the portion of the hub member is compressed radially inward. The method further includes configuring the connection features to engage one or more further connection features on a housing to attach the hub member to the housing when the connection features are in the first position, and to disengage the one or more further connection features on the housing to release the hub member from being attached to the housing when the connection features are moved a definable distance toward the second position.

In certain further examples of the method, the plurality of connection features on the hub member comprise a plurality of feet or protrusions extending radially outward relative to the axis.

BRIEF DESCRIPTION OF THE DRAWINGS

The above and other aspects and features of the present invention will become more apparent to those skilled in the art from the following detailed description of the example embodiments with reference to the accompanying drawings, in which.

DETAILED DESCRIPTION

Figure 1:
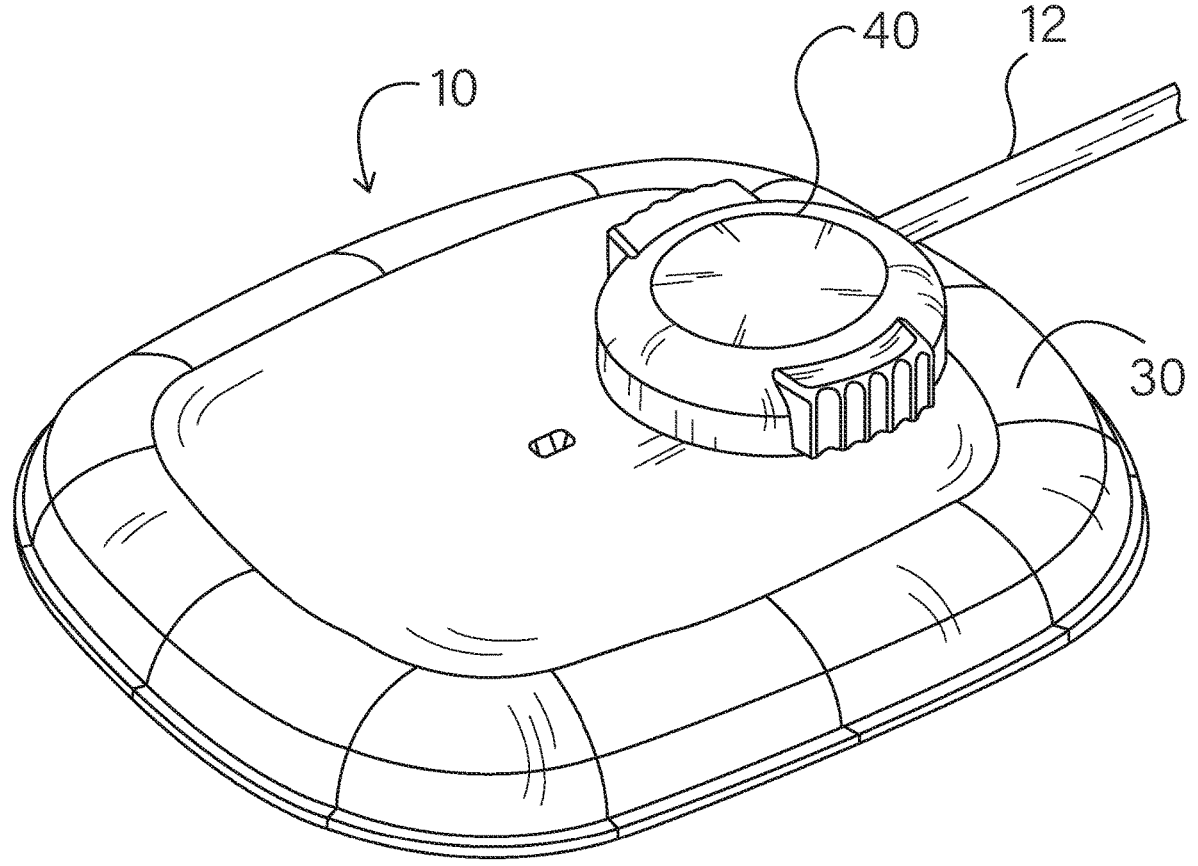
FIG. 1 is a perspective view of an example of an infusion set.

Hereinafter, example embodiments will be described in more detail with reference to the accompanying drawings. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated. Further, features or aspects within each example embodiment should typically be considered as available for other similar features or aspects in other example embodiments.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

It will be understood that when an element or feature is referred to as being "on," "secured to," "connected to," or "coupled to" another element or layer, it can be directly on, connected to, or coupled to the other element or feature, or one or more intervening elements or features may be present. In addition, it will also be understood that when an element or features is referred to as being "between" two elements or features, it can be the only element or feature between the two elements or features, or one or more intervening elements or features may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," "has," "have," and "having," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Example embodiments relate to infusion devices, infusion sets, injection ports, insertion sets, media delivery systems, sensors or other medical devices and systems (each generally referred to herein as a medical device or medical system) that connect (or are configured to connect) a subcutaneously insertable cannula or needle in fluid flow communication with one or more fluid flow conduits. The fluid flow conduit may be further connected to a fluid pump and reservoir system, or other fluid supply or processing system. In certain examples, the medical device or medical system is configured to facilitate providing one or more individual subcutaneous injections, or continuous subcutaneous injection of a medication or other infusion media. Other examples relate to methods of making and using such medical devices and medical systems.

Figure 2:
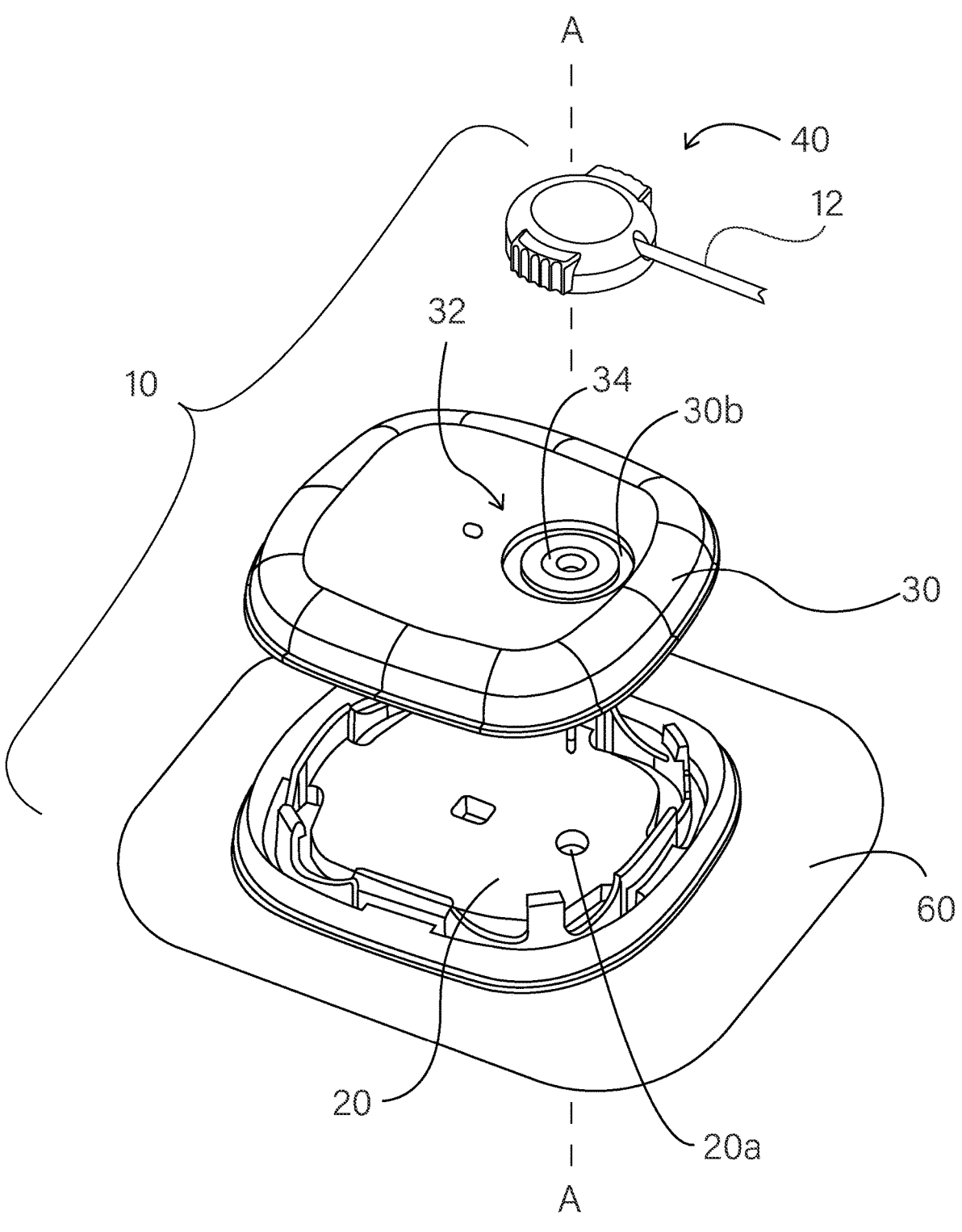
FIG. 2 is a partially exploded view of the infusion set of FIG. 1, with certain components separated along an axis A.
Figure 3:
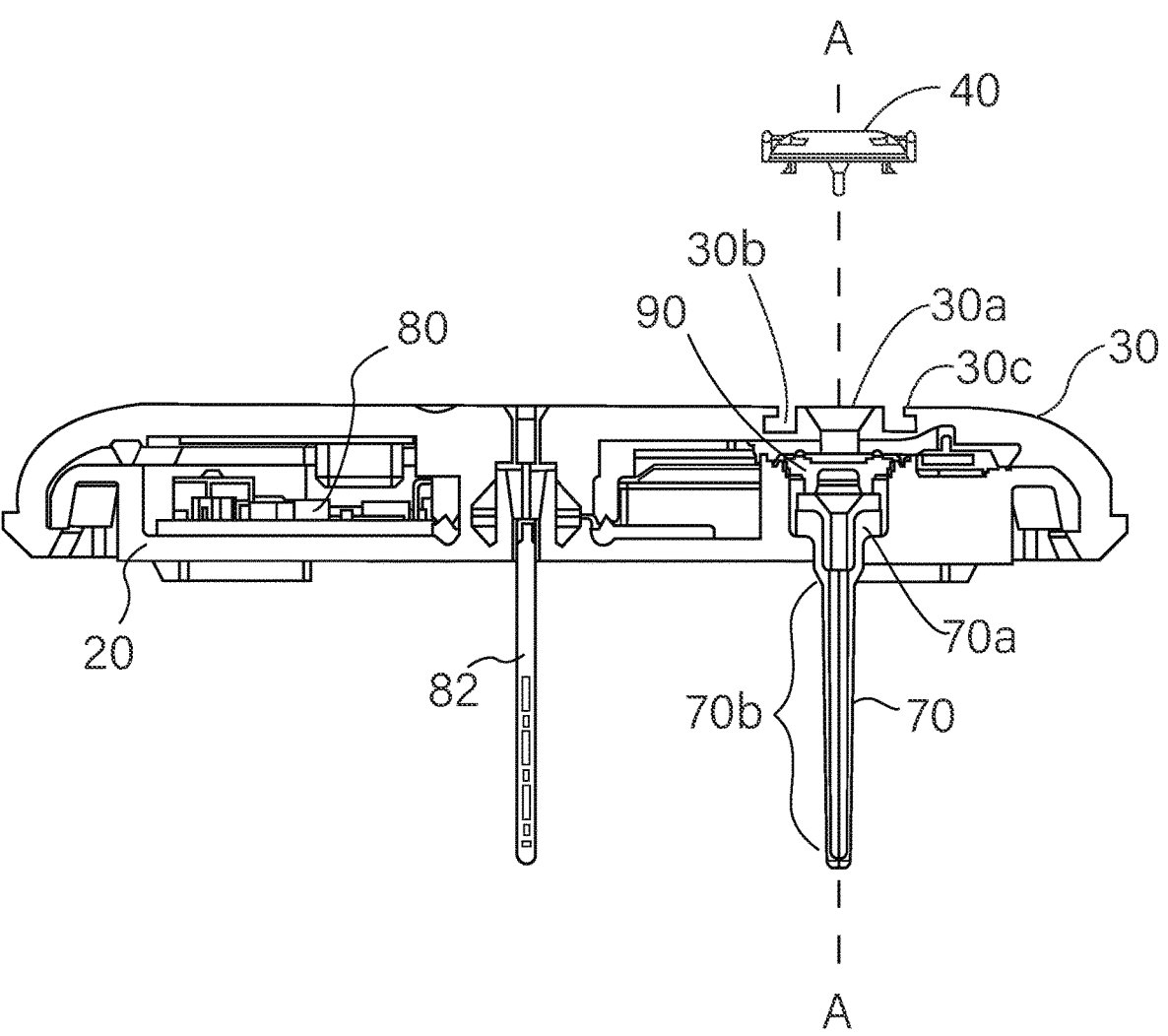
FIG. 3 is a cross-section view of the base, top member and cannula of the infusion set of FIG. 1.

An example of an infusion set system 10 is shown in FIGS. 1-3. The infusion set system 10 includes a base 20, a top shell member 30 and an infusion hub member 40. The base 20 is adapted to receive and connect with the top shell member 30. In addition, the infusion hub member 40 is configured to connect to the top shell member 30. The infusion set system 10 is shown in an assembled state in FIG. 1 and in an exploded view in FIG. 2. A cross-section view of the assembled base 20 and top shell member 30, with the infusion hub member 40 separated therefrom along the axis A, is shown in FIG. 3.

Figure 4:
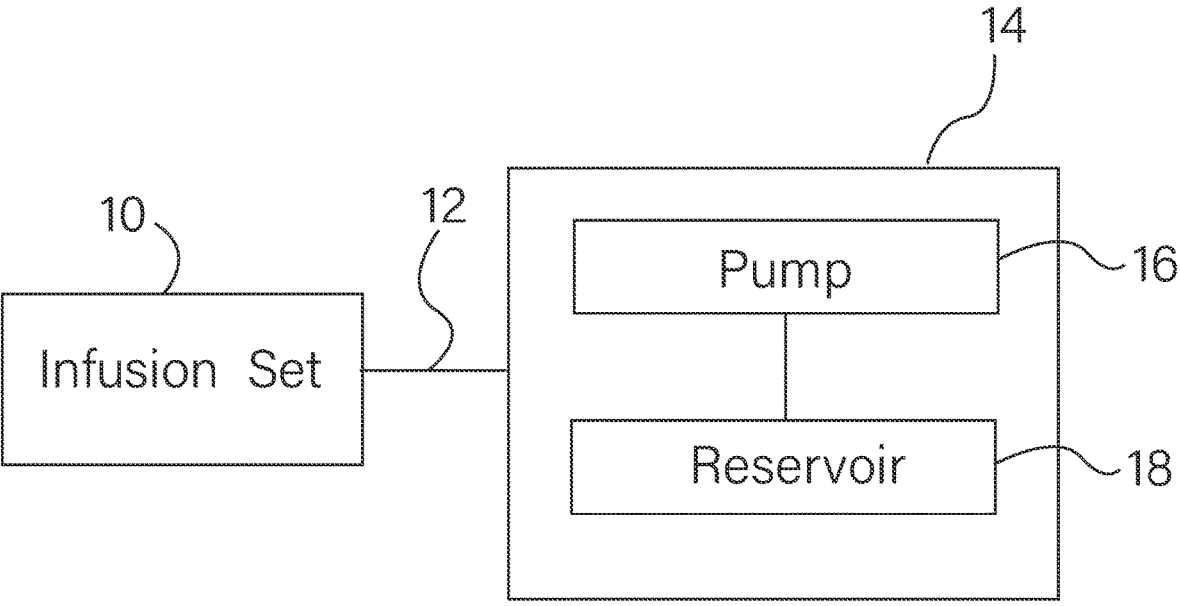
FIG. 4 is a schematic diagram of a system that includes an infusion set of FIG. 1.

When assembled, as shown in FIG. 1, the infusion set system 10 is configured to connect, through a fluid flow conduit 12 (such as, but not limited to a medical grade tubing) to an infusion media supply system 14. As represented in the diagram of FIG. 4, the infusion media supply system 14 may include a reservoir 16 that contains an infusion media and a pump 18 that is connected to deliver the infusion media from the reservoir to the conduit 12 (e.g., into an end of the conduit 12 that is not in view in FIGS. 1 and 2). In other examples, the infusion media supply system 14 may include a gravity-operated supply such as, but not limited to an intravenous bag or an infusion bag connected to the conduit 12. The conduit 12 is connected to deliver (and delivers) the infusion media to the infusion system 10, through the hub member 40 as described herein. As further described herein, the infusion set 10 includes a cannula that is insertable through the skin of a patient, and is connected to receive infusion media from the hub member 40, for delivery to the patient.

More specifically, the base 20 includes a generally rigid or semi-rigid body that is configured to be arranged on or secured to a patient's skin. In the illustrated example, the base 20 has a generally flat, plate-like configuration with an opening 20a through a bottom wall of the base, for a cannula. The base may have any suitable shape and, in particular examples, is configured to have a generally low profile in the axial dimension A. The base 20 may be made of any suitable material or materials including, but not limited to plastic, metal, ceramic, composite material, or combinations thereof.

In some examples, the base 20 includes an adhesive material layer 60. The adhesive material layer 60 may be secured to a surface on a first side of the base 20 (the downward-facing side in FIGS. 1-3) and has an adhesive material that may be selectively exposed to adhere the base 20 to a surface of a patient's skin, at a desired infusion site. The adhesive material layer 60 may be secured to the base 20 by any suitable securing mechanism including, but not limited to a glue or other bonding agent, thermal bonding, sonic welding, or the like.

In certain examples, a backing or release material layer (not shown) is adhered to the adhesive material layer 60 to cover and protect the adhesive material layer 60 from exposure to dirt or other environmental contaminants before adhering the base 20 to a patient's skin. In those examples, the release material layer is selectively removable from the adhesive material layer 60 to expose the adhesive material for adhering the base 20 to the patient's skin. In other examples, the adhesive material layer 60 and the release material layer may be omitted from the system 10. Alternatively or in addition, in further examples, the base 20 may include other suitable mechanisms for securing the base 20 to a patient's skin including, but not limited to bands, straps, sutures, suture eyelets for receiving sutures, or combinations thereof.

The base 20 also includes a first connection structure that connects to second connection structure (not shown) on the top member 30, to connect the base 20 and the top member 30 together, as shown in FIG. 3. The connection structures may include any suitable connection mechanism such as, but not limited to a friction fit, one or more clips or other fasteners, adhesive material or combinations thereof.

The top member 30 includes a generally rigid or semi-rigid body that is configured to be arranged on and secured to the base 20, via the connection structures, as shown I FIG. 3. In the illustrated example, the top member 30 has a generally flattened dome-shaped configuration. The top member 30 may have any suitable shape and, in particular examples, is configured to have a generally low profile in the axial dimension A. The top member 30 may be made of any suitable material or materials including, but not limited to plastic, metal, ceramic, composite material, or combinations thereof.

In particular examples, the base 20 and the top member 30 connect together in a clam-shell housing arrangement and, when connected together, define an interior volume in which various components of the infusion set system may be contained. In particular examples one or more of such components may be attached to or in the top member 30. In certain examples, the components in the housing may include sensor electronics 80 connected to an insertable sensor probe 82. In other examples, the sensor electronics 80 and probe 82 may be omitted. The housing contains and holds a portion of a cannula 70, while a further portion of the cannula 70 extends out through an opening in the bottom of the base 20. The further portion of the cannula 70 extends out from the first side (the downward-facing side in FIGS. 1-3) of the base 20, as shown in FIG. 3.

In certain examples, the top member 30 may carry and hold the cannula 70. In other examples, the cannula 70 may be carried and held by the base 20. In that regard, the top member 30 or the base 20 (or the combination thereof) includes a receptacle configured to receive and retain a collar 70a of the cannula 70. The receptacle may include one or more connection feature for securing the collar 70a of the cannula 70 in the receptacle such as, but not limited to a friction fitting, a clip or other fastener, adhesive material or combinations thereof. The receptacle may be located within the interior volume of the housing defined by the base 20 and the top member 30, when connected together.

The top member 30 includes a hub connection port 32 (described below). The connection port 32 includes an opening 30a through the top member 30, where the opening 30a is aligned with an open end of the collar 70a of the cannula 70 when the top member 30 is connected to the base 20, as shown in FIG. 3. The top member 30 or the base 20 (or both) define a channel between the opening 30a and the open end of the collar 70a of the cannula 70. A septum 90 may be located within the channel 70, to seal the open end of the collar 70a.

In certain examples, the septum 90 is configured to be pierced and is made of a pierceable material. In other examples, the septum 90 is a pre-pierced septum that has one or more slits, holes or cuts formed through the septum material. In those or other examples, the septum 90 may be configured as a self-sealing septum, for example, made of a substantially resilient material biased toward a sealed position. In some examples, the septum 90 is made of a molded disc of silicon, polyurethane or other appropriate material which can be secured to a wall or walls of the channel (in the base 20 or in the top member 30) in which it is disposed. The septum 90 may be secured by any suitable securing mechanism including, but not limited to adhesive, bonding, thermal bonding, sonic welding, or the like. In alternative examples, a suitably resilient material such as silicone, polyurethane, or other suitable elastomeric material can be molded directly into the channel. Alternatively or in addition to the septum 90, other examples may include one or more mechanical check-valves or other seals configured to provide a re-sealable fluid pathway in the channel.

A length portion 70b of the cannula is configured to extend through the opening 20a in the base 20, and out from the first side of the base 20 (the bottom side in the orientation of FIGS. 1 and 2), when the cannula collar 70a is received in the receptacle. When or after the base 20 is secured to the patient's skin, the top member 30 may be attached to the base 20, such that the cannula 70 extends through the opening 20a in the base 20 and into the patient's skin. Accordingly, when adhered to the patient's skin, the infusion set system 10 is configured to maintain the cannula 70 within the patient, while infusion media is delivered to the patient, through the cannula.

The cannula 70 may be made of a material that is compatible with fluids intended to be conveyed through the infusion device system 10, and with other materials to which the cannula may come into contact or be connected, in the intended environment of use. In certain examples, the cannula 70 is made of a material that is biologically compatible, for use in contexts in which the cannula is in contact or connected with a biological entity (such as a human patient or another biological entity), or is implanted fully or partially in the patient (or other biological entity). In certain examples, the cannula 70 is treated in one or more processes for enhancing biologically compatible such as, but not limited to cleaning, sterilizing, coating with Heparin, or the like.

The cannula material may be selected to be compatible with and suitable for conveying one or more desired or predefined fluids (such as, but not limited to insulin, cancer or AIDs treatment media, pain treatment media, or other medications, drugs or therapy fluids). Such materials may include, but are not limited to an ethylene tetrafluoroethylene (ETFE), a polytetrafluoroethylene (PTFE), a fluorinated ethylene propylene (FEP), a perfluoroalkoxy (PFA), a polychloroprene (Neoprene), a polypropene (PP), a polypropylene, a polyethylene (PE), a fluorinated ethylene propylene (FEP) or other fluoropolymer, an ethylene vinyl acetate (EVA), a polyether block amide (PEBA) of thermoplastic elastomer (TPE) such as PEBAX™, a thermoplastic polyurethane (TPU) such as PELLETHAN™, a silicon material, other fluoropolymer, synthetic rubber, thermoplastic polymer, or the like. However, for other contexts and applications of use, the cannula 70 may be made of other materials suitable and compatible with those contexts and applications. In certain examples, the cannula 70 could be a substantially hard or rigid cannula material or a hypodermic needle. The cannula 70 may be made by any suitable manufacturing process including, but not limited to extrusion, molding, machining, or combinations thereof.

The length portion 70b of the cannula 70 may have a length (along the axial dimension A) that is selected for a desired application of use. Various examples may include different lengths to accommodate differences in the desired depth to which the cannula extends within a patient. In some examples, the cannula 70 has a length to extend into a subcutaneous fat layer of a patient. In other examples, the cannula 70 has a length to extend beyond the subcutaneous fat layer. In certain examples, the cannula length for a patient is selected based on the amount of subcutaneous fat. For example, the length portion 70b of the cannula 70 can have a length in the range of from about ¼" to about 2". In other examples, the length portion 70b of the cannula 70 has a length outside of that range.

In certain examples, the base 20 may be secured to the patient's skin, for example, by pealing the release layer from the adhesive material layer 60 and then pressing the exposed adhesive material layer 60 against the patient's skin at a desired infusion site. In some examples, the cannula 70 is initially connected to a receptacle in the top member 30. Then, after the base 20 is secured to the skin, the cannula 70 is inserted into the patient's skin (by passing the length portion 70b of the cannula through the opening in the base 20, simultaneously with the action of moving the top member 30 into connection engagement with the base 20. In other examples, the cannula 70 is connected to a receptacle on the base 20, and may inserted into the patient's skin, simultaneously with the action of pressing the adhesive material layer 60 against the patient's skin. In yet other examples, the cannula may be inserted into a receptacle on the base 20 and into the patient's skin, at a time after the base 20 is secured to the patient's skin and before the top member 30 is engaged and connected to the base 20. In yet other examples, the base 20 and the top member 30 are connected together before the base is secured to the skin and before the cannula is inserted into the skin.

In any of those examples, the cannula 70 (or the cannula 70 and one or both of the base 20 and the top member 30) may be inserted through the opening 20a of the base 20 and into the patient's skin, by an insertion tool that includes an introducer needle. In those examples, the cannula 70 may be initially supported on the introducer needle, with the introducer needle 32 extending coaxially with the cannula 70 (e.g., either inside of the central channel of the cannula 70 or with the cannula inside of a central channel of the introducer needle). In that arrangement, the introducer needle extends beyond the distal end of the cannula 70 to provide a rigid, sharp insertion tip. Accordingly, while the base 20 is engaged or secured to the patient's skin by the adhesive material layer 60 (or other securing mechanism), the introducer needle may pass through the opening 20a in the base 20, pierce the skin and be inserted (with the cannula) into the patient's skin. As the introducer needle and cannula are inserted into the skin, the collar 70a of the cannula 70 may be received and secured to the receptacle in the base 20 or the top member 30 (or both). Then, the introducer needle may be withdrawn from the cannula 70, while leaving the cannula in an inserted state.

In some examples the cannula may be inserted into the patient's skin by an insertion tool that moves an introducer needle and the cannula under the force of a spring or other force-imparting mechanism and then withdraws the introducer needle while leaving the cannula in the patient's skin. In certain examples, the insertion tool may carry and hold the top member 30, or both the top member 30 and the base 20, and may move the top member 30 into engagement with the base 20, engage and secure the base 20 to the patient's skin, and move the insertion needle and the cannula into the patient's skin in a single (or a plurality) of actions.

Once the infusion device system 10 is secured to a patient's skin with the cannula inserted into the patient's skin (and the inserter needle withdrawn), the hub member 40 may be connected to the top member 30. In some examples, the hub member 40 is connected to the top member by an insertion tool, for example, in the same action in which the tool engages and connects the top member 30 to the base 20. In other examples, the hub member 40 is connected to the top member 30 (e.g., manually or by an insertion tool) after the cannula 70 is inserted, and after the top member 30 is secured to the base 20.

The top member 30 may have a generally flat surface (the upper surface in FIGS. 1-3) on which the connection port 32 is provided for connection of the hub member 40. In particular examples, the connection port 32 is configured to interface with the hub member 40 and provide a releasable connection that allows the hub member 40 to engage the connection port 32 and be selectively connected and disconnected from the top member 30 with a relatively simple, manual squeezing action. Additionally or alternatively, the connection port 32 is configured to allow rotation of the hub member 40 about the axis A, when the hub member 40 is engaged with the connection port 32.

Figure 5:
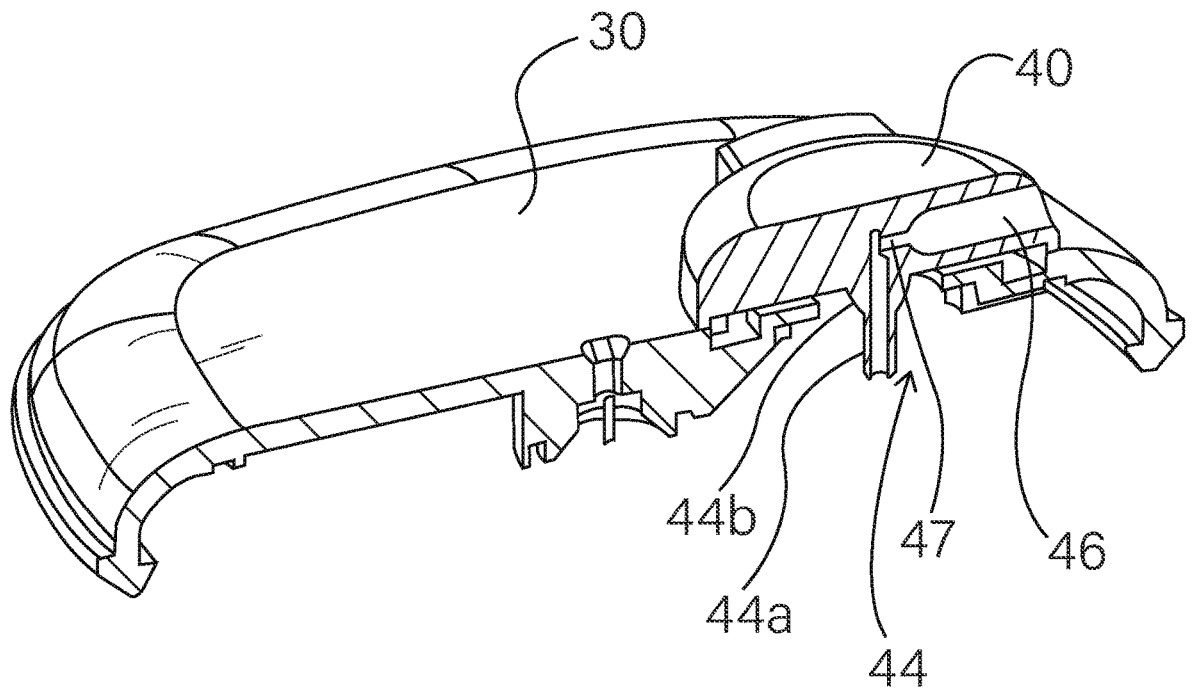
FIG. 5 is a cross-section view of the top member and the hub member of the infusion set of FIG. 1.
Figure 6:
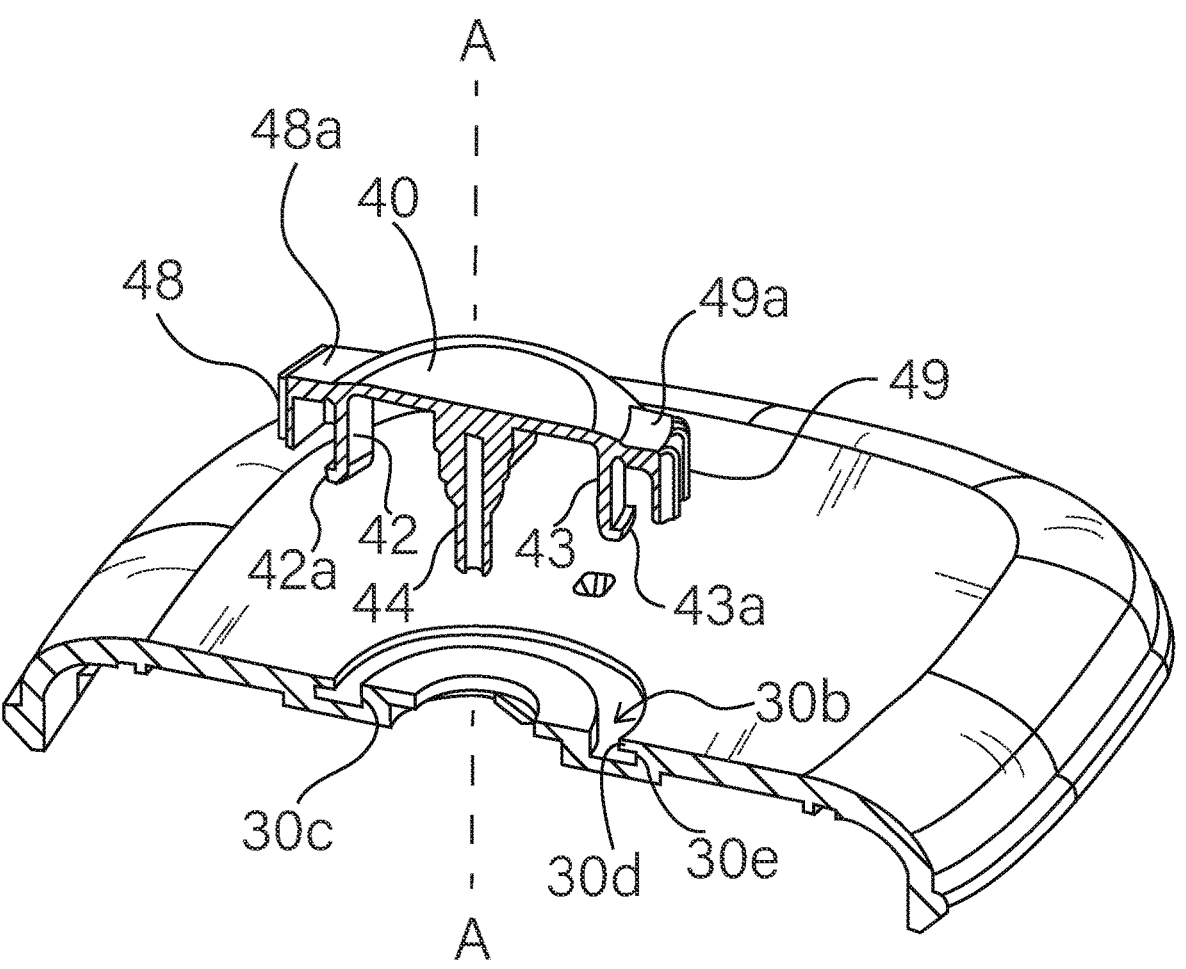
FIG. 6 is a cross-section, exploded view of the top member and the hub member of the infusion set of FIG. 1.
Figure 7:
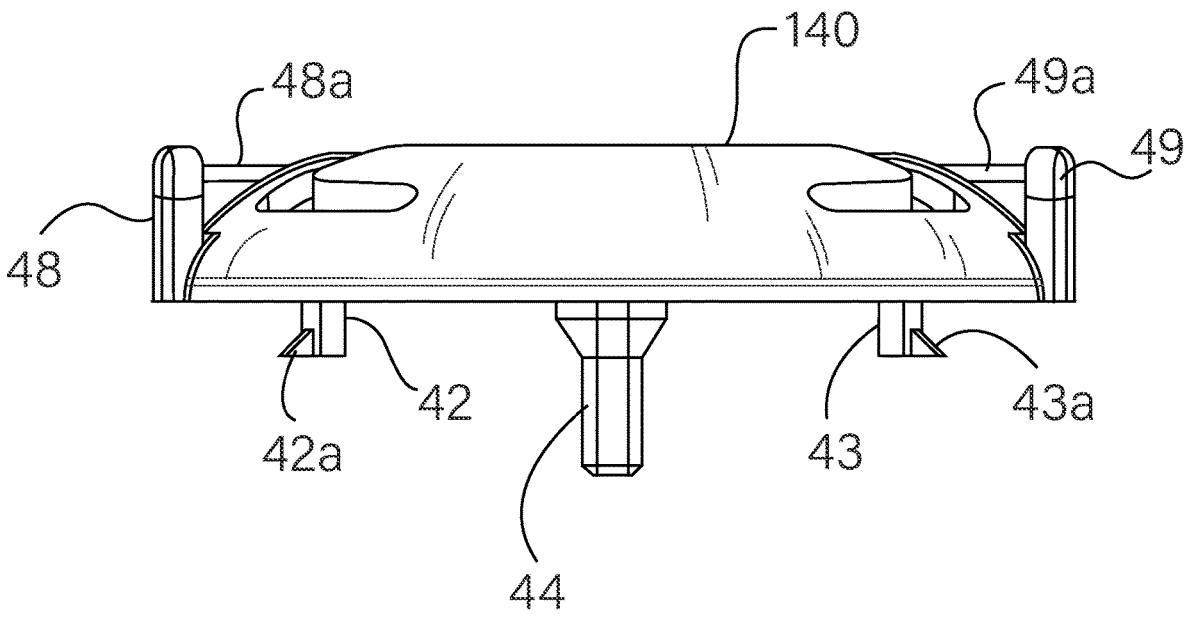
FIG. 7 is a side view of another example of a hub member.
Figure 8:
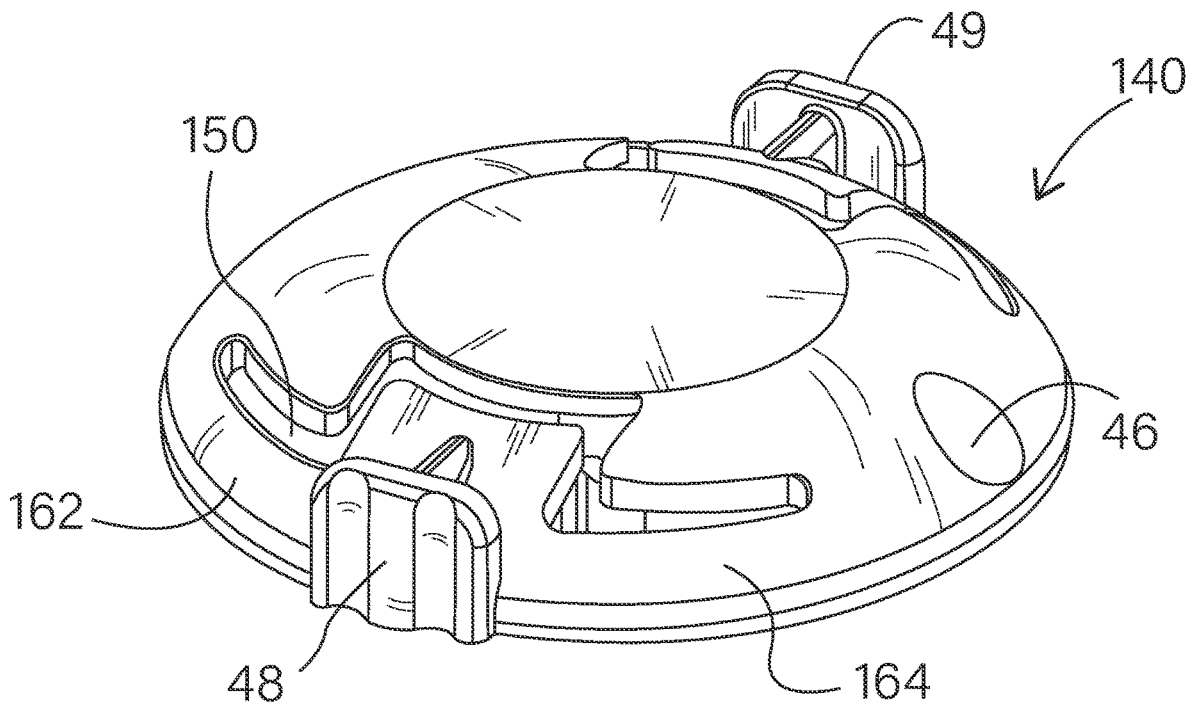
FIG. 8 is a perspective view of the hub member of FIG. 7.
Figure 9:
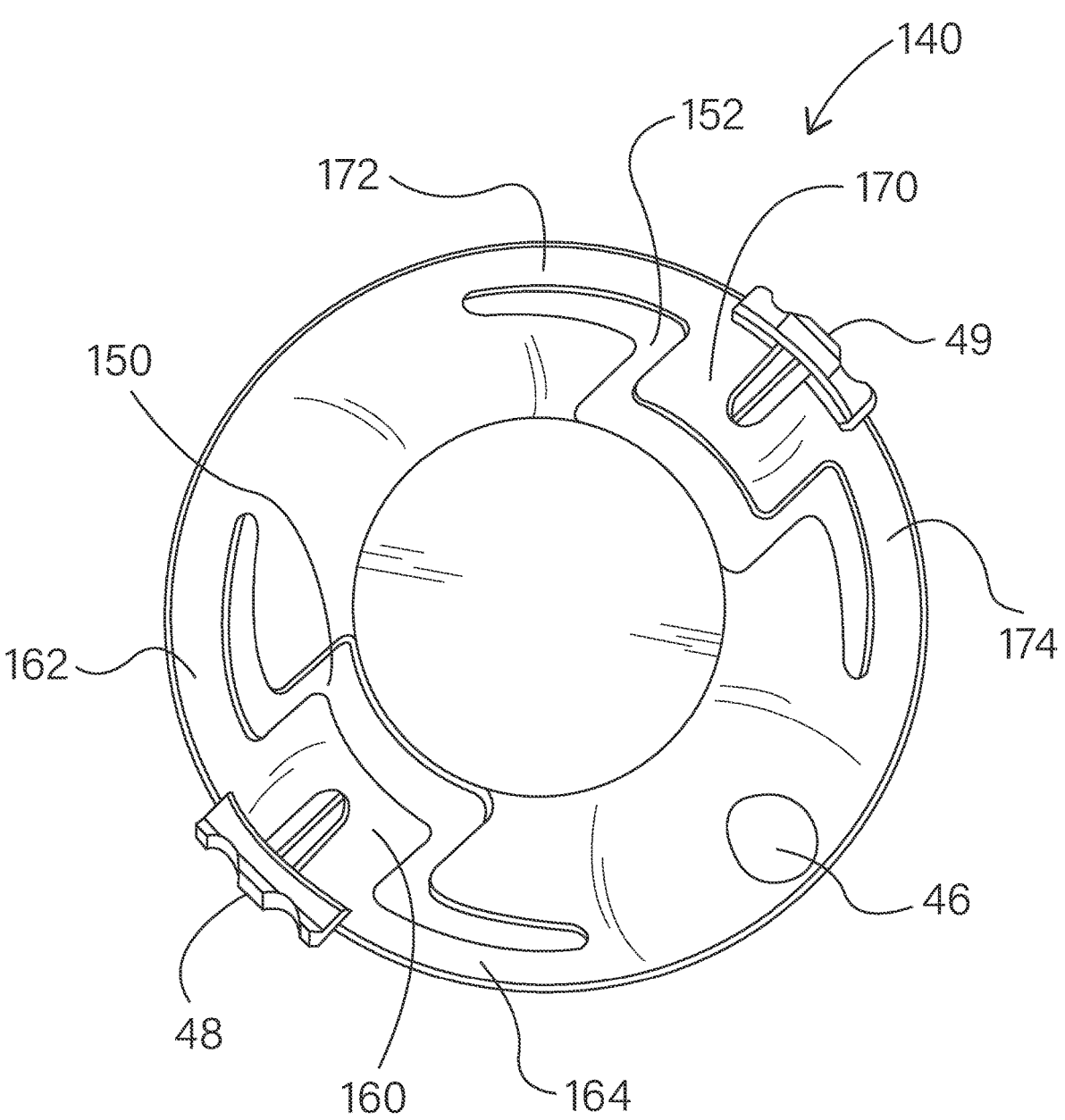
FIG. 9 is a top view of the hub member of FIG. 7.

Cross-section views of an example of the top member 30 and the hub member 40 are shown in FIGS. 5 and 6. The cross-section views in FIGS. 5 and 6 are perpendicular to each other, and cross the center of the connection port 32 in the top member 30. FIG. 5 shows the hub member 40 assembled together with the top member 30, while FIG. 6 shows an exploded view, with the hub member 40 separated from the top member 30 along the axis A.

The connection port 32 includes an annular recess or groove 30b provided in the generally flat upper surface of the top member 30. The annular recess or groove 30b surrounds and is coaxial with the opening 30a. The annular recess or groove 30b has a round or circular shape to provide a circular guide for rotational movement of the hub member 40, while the hub member 40 is engaged with the connection port 32 on the top member 30.

The annular recess or groove 30b in the top member 30 is configured to receive two extensions or legs 42 and 43 of the hub member 40, when the hub member 40 is engaged with the connection port 32. In particular examples, the annular recess or groove 30b defines an outer peripheral wall 30e and an inner peripheral wall 30c, as shown in FIGS. 5 and 6. The outer peripheral wall 30e includes one or more securing features that engage with one or more securing features 42a and 43a on each of the legs 42 and 43 of the hub member 40 to secure the hub member 40 to the top member 30, when the hub member 40 is engaged with the connection port 32. In one example, the one or more features on the outer peripheral wall 30e include an annular (or partially annular) lip or ledge 30d that extends over a portion of the annular recess or groove 30b and around (or partially around) the annular recess or groove 30b. In other examples, the one or more features on the outer peripheral wall include one or more (or a plurality of) slot-shaped openings (instead of an annular lip) in the outer peripheral wall 30e that receive the one or more features 42a and 43a on the legs 42 and 43 of the hub member 40.

The hub member 40 includes a generally rigid or semi-rigid body. In the illustrated example, the hub member 40 has a generally disc-shaped cap configuration, with the legs 42 and 43 and a cannula 44 extending from one side (the downward-facing side in FIGS. 5 and 6). The cannula 44 may be rigid or semi-rigid (more rigid than the cannula 70). While the illustrated example shows a generally disc-shaped hub member 40, in other examples the hub member 40 may have any other suitable shape. In particular examples, is configured to have a generally low profile in the axial dimension A. The hub member 40 may be made of any suitable material or materials including, but not limited to plastic, metal, ceramic, composite material, or combinations thereof. In particular examples, the hub member 40 is made of a material that is rigid enough to hold its shape and function as described herein, but also has sufficient flexibility and resiliency to allow the hub member 40 (or a portion of the hub member 40) to be squeezed and compressed in a radially inward direction (transverse to the axis A) when a squeezing force is applied, and to resiliently return to its un-squeezed shape, when the squeezing force is removed, as described herein. Such materials may include, but are not limited to polypropylene, polyester, co-polyester, polycarbonate, polycarbonate/co-polyester alloys, acetal, or the like.

In particular examples, the hub member 40 is made of a single, unitary body that has features as described herein formed, for example, by molding, machining or other suitable manufacturing method. An example hub member 40 configuration suitable for forming as a single unitary structure is shown in FIGS. 5 and 6 (or as shown with regard to hub member 140, 240 or 340 in FIGS. 7-13). However, in other examples, the hub member may be made of multiple components that are attached together, for example, by adhesive, welding, heat staking, fasteners or other connection mechanism.

The hub member 40 has a port 46 that connects to the conduit 12 (not shown in FIGS. 5 and 6, but shown connected to the port 46 in FIGS. 1 and 2).

The conduit 12 can be secured to the port 46 by any suitable process or mechanism as desired. In certain examples, the port 46 tapers in diameter from an open, outer end to a fluid channel 47 in the body of the hub member 40. This taper can provide for a tight press-fit, allowing the conduit 12 to be retained by friction fitting with the inner wall of the port 46. Alternatively or in addition, the conduit 12 can be secured in the port 46 by adhesives, welding, thermal connection, Luer connector or other tubing connector, or any other suitable connection mechanism.

The port 46 is connected in fluid flow communication with the cannula 44, by the fluid channel 47 in the body of the hub member 40. The cannula 44 has a fluid flow channel that is in fluid flow communication with the fluid channel 47 at one end, and is open on the distal end (the lower end in FIGS. 5 and 6) of the cannula 44. Accordingly, when the conduit 12 is connected to the port 46 (as shown in FIGS. 1 and 2), the open distal end of the cannula 44 may be connected in fluid flow communication with the media supply system 14, through the conduit 12, the port 46, the fluid flow channel 47 and the fluid flow channel in cannula 44.

The inner diameter of the fluid flow channel of the cannula 44 may be selected to allow a sufficient fluid flow rate for a desired application of use. In some examples, the flow channel of the cannula 44 has an internal diameter of between about 0.01" and about 0.03". Other examples have diameters outside of that range.

The cannula 44 has a shape that is configured to be received in, and extend through the septum 90, when the hub member 40 is connected with the connection port 32 on the top member 30. The cannula 44 has sufficient column strength to be inserted through the septum 90 (or other sealing member). Thus, the cannula 44 may be made of a rigid or semi-rigid material such as PVC, PET, nylon, stainless steel, or other material suitable for use in medical applications and having sufficient rigidity. In other examples, the cannula 44 is formed integral with the rest of the body of the hub member 40 and is made of the same material as the body of the hub member 40.

In particular examples, the septum 90 is configured to provide a seal around the cannula 44. The cannula 44 includes a first length portion 44a and a second length portion 44b, where the first length portion 44a extends from the distal end of the cannula to the second length portion 44b. The second length portion 44b couples the first length portion 44a of the cannula 44 to the rest of the hub member 40, and couples the fluid flow channel in the cannula 44 into fluid flow communication with the channel 47.

The outer diameter of the first length portion 44a of cannula 44 may selected to be sufficiently small to reduce wear on the septum 90 and reduce the insertion force needed to insert the cannula 44 through the septum 90, yet be large enough to allow for an inner fluid flow channel of sufficient size for a desired fluid flow rate, and a cannula wall thickness that provides strength and durability suitable for the desired application of use. The second length portion 44b may flare or taper outward relative to the first length portion 44a such that the outer diameter of the second length portion 44b is larger than the outer diameter of the first length portion 44a. The larger outer diameter of the second length portion 44b allows the second length portion 44b to have a greater wall thickness, which can increase the strength and durability of the cannula 44.

In particular examples, the connection port 32 in the top member 30 forms (or includes) a cannula guide 34 (shown in FIG. 2) that is configured to receive the cannula 44, when the hub member 40 is engaged with the connection port 32 on the top member 30. The cannula guide 34 may be an annular body of generally rigid material such as, but not limited to plastic, metal, ceramic, composite material or combinations thereof, and may be connected to the top member 30 by any suitable connection mechanism such as, but not limited to adhesives, welding, thermal bonding, fasteners or the like. In other examples, the cannula guide 34 may be omitted or may be formed integrally with (and as part of) the top member 30. The cannula guide 34 has a central opening aligned with the opening 30a of the port 32.

The central opening of the cannula guide 34 has a size and shape that receives and engages the outer peripheral surface of the second length portion 44b of the cannula 44, when the hub member 40 is connected with the connection port 32 (and, thus, when the first length portion 44a of the cannula 44 is extended through the septum 90). In certain examples, the engagement of the second length portion 44b of the cannula 44 with the cannula guide 34 provides a snug fit between those features, such as, but not limited to a sealing engagement or a friction fit. The flared or tapered transition of the second length portion 44b of the cannula 44 can help to guide the cannula 44 into the cannula guide 34 (and the septum 90). In some examples, the central opening of the cannula guide 34 may be flared or tapered to a larger diameter at the top end, to help guide the cannula 44 into the cannula guide 34 (and the septum 90), when the hub member 40 is brought into engagement with the connection port 32 on the top member 30.

As discussed above, the hub member 40 includes two legs 42 and 43, each having one or more connection features 42a and 43a that engage with one or more further connection features 30d on the outer peripheral wall 30e of the connection port 32, to secure the hub member 40 to the connection port 32 (and to the top member 30) when the hub member 40 is connected with the connection port 32 (and, thus, when the cannula 44 is inserted through the septum 90). Each connection feature 42a and 43a include at least one foot (or protrusion) extending radially outward, transverse to axis A.

In particular examples, the legs 42 and 43, or the portion of the body of hub member 40 (or both) are made of a material and configuration to be sufficiently flexible and resilient to flex and move slightly in the radially-inward direction when a squeezing force is applied to the outer surface of the hub member 40, adjacent the legs 42 and 43. In addition, the legs 42 and 43 or the portion of the body of the hub member 40 (or both) are configured to resiliently flex and move back outward in the radially-outward direction, when the squeezing force is removed. In that manner, the legs 42 and 43 may have a first position or state when no squeezing force is applied, and may be moved to or toward a second position or state (radially inward relative to the first position or state) when a squeezing force is applied. As discussed herein, the squeezing force may be applied manually or by a tool.

When a squeezing force is applied (and the legs 42 and 43 are in the second position or state), the hub member 40 may be arranged to engage the connection port 32, with the legs 42 and 43 of the hub member 40 fit at least partially into the annular groove 30b of the connection port 32. While the squeezing force is applied, the connection features 42a and 43a on the legs 42 and 43 may be free or clear of the connection features 30d on the outer peripheral wall 30e of the connection port 32. From that state, the squeezing force may be released to allow the legs 42 and 43 to resiliently move back outward, toward the first position or state. As the legs 42 and 43 move radially outward toward the first position or state, the connection features 42a and 43a engage with corresponding connection features 30d on the outer peripheral wall 30e of the connection port 32.

When the connection features 42a and 43a on the legs 42 and 43 are engaged with the connection features 30d on the outer peripheral wall 30e, the connection features retain and secure the hub member 40 to the connection port 32 (and to the top member 30). In particular examples, the legs 42 and 43 and the connection features 30d provide a sufficiently strong connection of the hub member 40 to the connection port 32 (and to the top member 30) to hold and maintain the hub member 40 on the top member 30 throughout a period of intended use of the infusion device system 10.

However, from that state, another squeezing force may be applied to the outer surface of the hub member 40, adjacent the legs 42 and 43, to move the legs 42 and 43 radially inward toward the second position or state and release the connection features 42a and 43a from the connection features 30d. In that released state, the hub member 40 may be withdrawn (e.g., lifted upward in the axial direction A) and removed (disengaged) from the connection port 32 and the top member 30, for example, for replacement, inspection or servicing of the hub member 40 of the connection port 32. Alternatively or in addition, the hub member 40 may be removed from the connection port 32, to allow access to the connection port by a syringe or other medical device (for insertion of the syringe or other medical device directly into the port 32 and through the septum 90) to deliver infusion media to the cannula 70 from the syringe or other medical device.

Alternatively or in addition, in the released state, the hub member 40 may remain engaged with the connection port 32 (with the cannula 44 extending into the port 32 and through the septum 90), and be selective rotated about the axis A to a desired position (e.g., to adjust the direction of the port 46 and the conduit 12). As the hub member 40 is rotated to an adjusted position, the legs 42 and 43 slide within the round, annular recess or groove 30b. Once the hub member 40 is rotated to a desired position, the squeezing force may be removed to re-engage the connection features 42a and 43a with the connection features 30d on the outer peripheral wall 30e, to retain the hub member 40 in the desired, adjusted position. In other examples, the connection features 30d on the outer peripheral wall 30e is configured to allow the hub member 40 to rotate (and the legs 42 and 43 to slide within the annular recess or groove 30b) while the connection features 42a and 43a remain engaged with the connection features 30d (e.g., with or without requiring the squeezing force to be applied).

The squeezing force to selectively release the connection features 42a and 43a from the connection features 30d may be applied manually, for example, by squeezing the hub member 40 between a finger and a thumb on one hand. In particular examples, the legs 42 and 43 are arranged on opposite sides of the axis A of the hub member 40, such that the hub member 40 may be easily gripped between a finger and thumb of one hand, to apply the squeezing force on opposite sides and directed radially inward (toward the axis A), to release the connection features.

In certain examples, the hub member 40 may include one or two finger or thumb grips or pads 48 and 49 positioned at locations at which the user may easily apply a finger or thumb for applying the squeezing force. In particular examples, the pads 48 and 49 are formed integral with the body of the hub member 40. In other examples, the pads 48 and 49 are formed separately from, and connected to the hub member 40. The pads 48 and 49 may be arranged on the body of the hub member 40 on opposite sides of the axis A. The pads 48 and 49 may be adjacent to or connected to the legs 42 and 43 such that a radially inward directed squeezing force on the pads causes a radially inward movement of the legs 42 and 43 toward the second position or state of the leg.

By arranging the pads 48 and 49 in relation to the legs 42 and 43 such that a radially inward-directed squeezing force on the pads causes the connection features 42a and 43a on the legs 42 and 43 to move in the same direction (radially inward), an natural feeling and easy-to-use mechanism may be provided for connecting and disconnecting the hub member 40 from the connection port 32 and the top member 30, or for releasing connection features to allow rotational adjustment of the hub member 40 about the axis A (or both). Because the action of releasing the connection features 42a and 43a is caused by moving the connection features 42a and 43a in the same direction as the direction of the squeezing force applied to the pads 48 and 49, the release of the connection features can be easily managed by typical users.

In certain examples, as shown in FIG. 6, the legs 42 and 43 are arranged at or adjacent the outer periphery of the generally disc-shaped body of the hub member 40, and the pads 48 and 49 are extended outward from the disc-shaped outer periphery, along the same diameter line as the legs 42 and 43 (referring to a diameter line extending along the cross-section plane of FIG. 6, perpendicular to the axis A). In that example, the pads 48 and 49 may include extension portions 48a and 49a, respectively, to position the pads 48 and 49 radially outward from the disc-shaped outer periphery of the hub member 40. In that arrangement, a radially inward-directed squeezing force on the pads 48 and 49 is transferred through the extension portions 48a and 49a, to cause the connection features 42a and 43a on the legs 42 and 43 to move radially inward and selectively release the connection features as described above.

In any of the examples described herein, the pads 48 and 49 may be located close to or on the disc-shaped outer periphery of the hub member 40. For example, the pads 48 and 49 in FIGS. 7-9 have a lower end connected to the disc-shaped outer periphery of the hub member 40, and an upper end connected to the rest of the body of the hub member 40 through extension portions 48a and 49a, respectively.

In the example in FIGS. 1-6, the legs 42 and 43 (and the connection features 42a and 43a) are arranged at or adjacent the disc-shaped outer periphery of the hub member 40. In other examples, the legs may be arranged radially inward of the outer periphery of the generally disc-shaped body of the hub member 40. For example, FIGS. 7-12 show hub members 140 and 240 with legs 42 and 43 located well within the outer periphery of the generally disc-shaped body of the hub member. FIGS. 7-12 have features labeled with reference numbers in a manner corresponding to reference numbers on similar features in FIGS. 1-6. Accordingly, the above description of those features (for FIGS. 1-6) also applies to the correspondingly numbered features in FIGS. 7-12.

In any of the examples described herein, the body of the hub member may include one or more cut-outs or openings that provide or increase flexibility of the hub member in response to a squeezing force applied to the pads 48 and 49. The example in FIGS. 7-9 includes cut-outs or shaped openings 150 and 152. Each cut-out or opening 150 and 152 partially surrounds and defines a leg-supporting section 160 and 170, respectively, that is connected to the rest of the body of the hub member 140 by two narrower sections 162 and 164, or 172 and 174. For example, each opening 150 or 152 has multiple portions that are linked, including straight portions and arcuate portions. As shown, in each opening 150 or 152, two straight portions are parallel and linked together via a center arcuate portion, and the two straight portions and the center arcuate portion surround and define edges of a respective one of the section 160 or 170. In each opening 150 or 152, the center arcuate portion is linked together with a side arcuate portion via a straight portion. An opening 150 or 152 includes a plurality of arcuate portions and a first straight portion that are linked. Two or more of the plurality of arcuate portions are linked together by the first straight portion. A first arcuate portion and a second arcuate portion of the plurality of arcuate portions are linked together by the first straight portion, and the first arcuate portion and a third arcuate portion of the plurality of arcuate portions are linked together by a second straight portion of the opening 150 or 152. The opening 150 or 152 further includes a second straight portion. The first straight portion and the second straight portion are parallel. A line normal to an edge of an arcuate portion (e.g., the center arcuate portion) of a plurality of arcuate portions, at a point on the edge of that arcuate portion, is parallel to an edge of the first straight portion and to an edge of the second straight portion. The legs 42 and 43 (and the connection features 42 *a* and 43 *a*) extend from the leg-supporting sections 160 and 170.

The narrower sections 162 and 164, or 172 and 174 are more flexible than other portions of the body of the hub member (e.g., due to their narrow structure or other aspects of their configuration or material). With that enhanced flexibility, the body of the hub member 140 may readily flex at the narrower sections 162 and 164 to move the hub member section 160 and 170 (and, thus, the legs 42 and 43) radially inward, in response to a squeezing force applied to the pads 48 and 49. Accordingly, the hub member 140 may operate in a manner similar to the hub member 40 described above with regard to FIGS. 1-6, to selective connect and disconnect from the connection port 32, and to be selectively rotatable, when engaged with the connection port 32.

Figure 10:
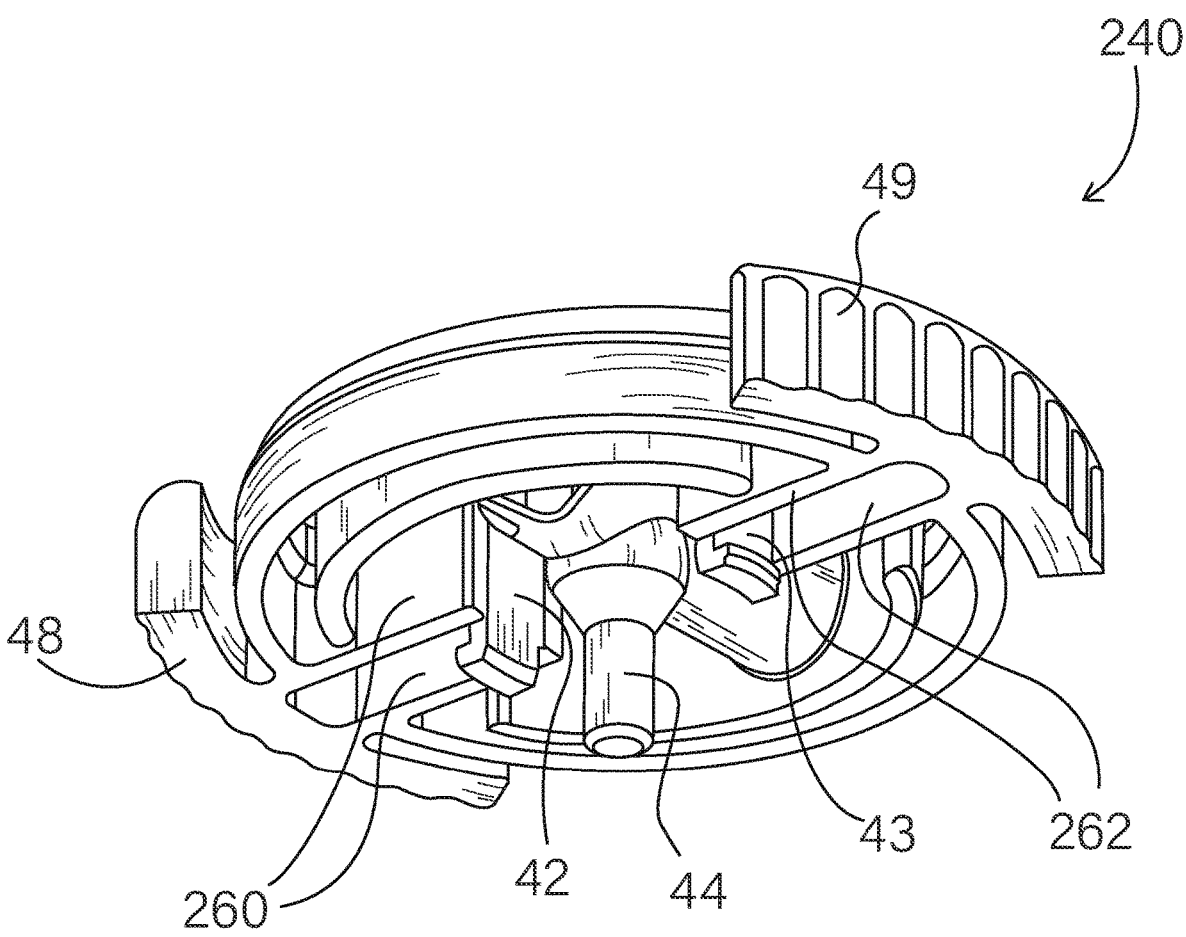
FIG. 10 is a perspective view of another example of a hub member.
Figure 11:
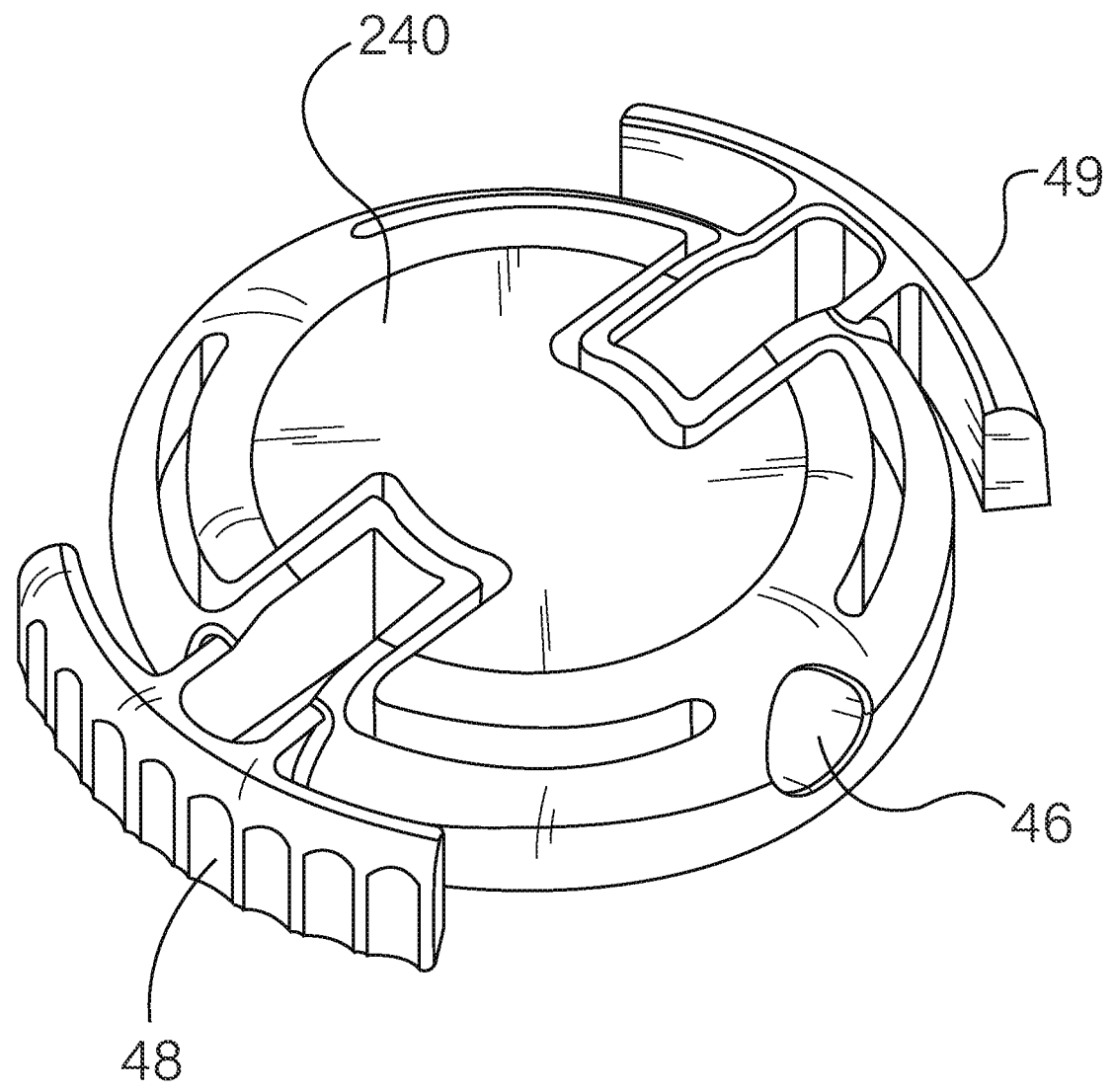
FIG. 11 is a perspective view of the hub member of FIG. 10.
Figure 12:
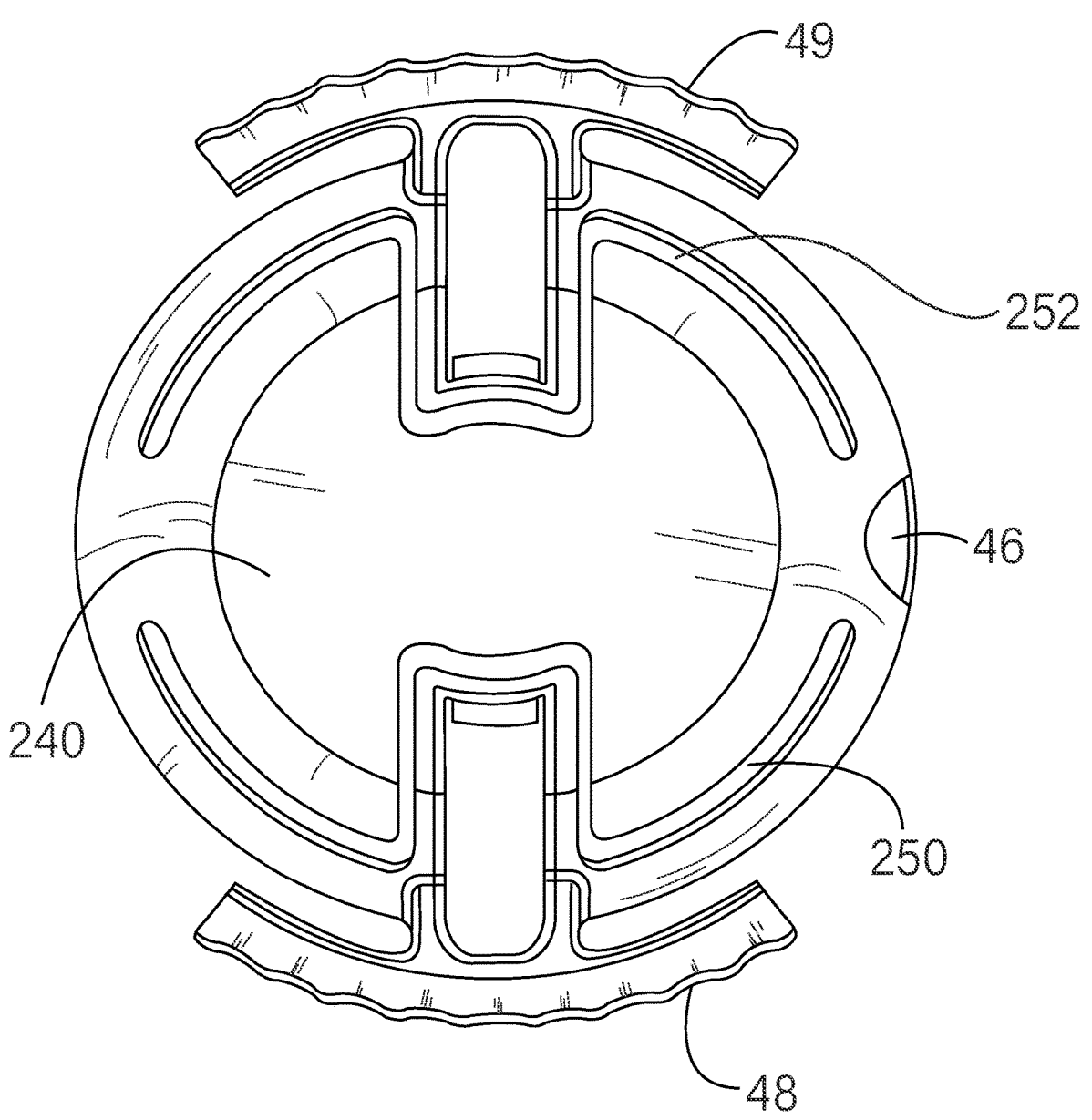
FIG. 12 is a top view of the hub member of FIG. 10.

The example in FIGS. 10-12 also includes cut-outs or shaped openings labeled 250 and 252. The cut-outs or shaped openings labeled 250 and 252 define narrow sections of the body of the hub member 240 (similar to narrow sections 162 and 164 described above) and moveable hub member sections 260 and 270 (similar to hub member sections 160 and 170 described above). However, in the example in FIGS. 10-12, the legs 42 and 43 are located closer to the cannula 44, relative to examples illustrated in FIGS. 1-9. In addition, the legs 42 and 43 are connected to the pads 48 and 49, respectively, by struts or walls 260 and 262 (corresponding to extension portions 48*a* and 49*a*), respectively, provided or formed within a disc-shaped cap body of the hub member 240.

Figure 13:
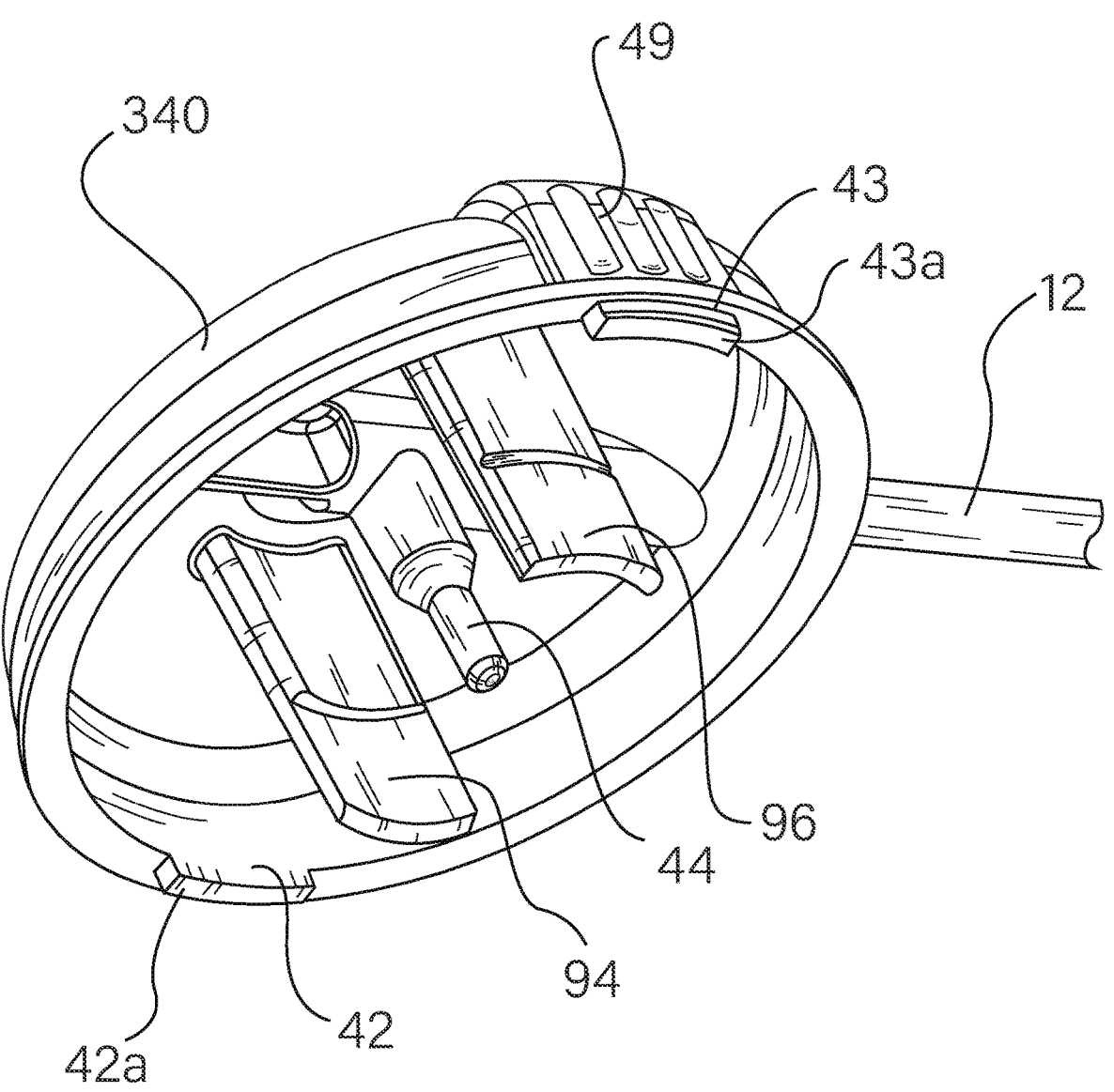
FIG. 13 is a perspective view of another example of a hub member.

In any of the examples described herein, the legs 42 and 43 may be omitted (or may be reduced in size) and the connection features 42*a* and 43*a* may be provided on or adjacent the outer periphery of the generally disc-shaped body of the hub member 40. The example hub member 340 in FIG. 13 has legs 42 and 43 of relatively small length, and connection features 42*a* and 43*a* on or adjacent the outer periphery of the generally disc-shaped body of the hub member 40. In addition, in the example of FIG. 13, the pads 48 and 49 are formed on the body of the hub member 40 without extension portions 48*a* and 49*a* described above. FIG. 13 have features labeled with reference numbers in a manner corresponding to reference numbers on similar features in FIGS. 1-12. Accordingly, the above description of those features (for FIGS. 1-12) also applies to the correspondingly numbered features in FIG. 13.

In any of the examples described herein, the cannula 44 may be surrounded or partially surrounded by wall sections of the hub member. For example, the cannula 44 in FIG. 13 is partially surrounded by cylindrical wall sections 94 and 96. In other examples, the cannula 44 is surrounded by additional wall sections or a fully cylindrical wall. The wall sections 94 and 96 or cylindrical wall can help protect the cannula 44 from contact with a user's fingers, or other objects that might contaminate its sterility. The cannula 44 can be positioned within the cylindrical wall or wall sections such that the cannula 44 is substantially co-axial with the cylindrical wall or wall sections. In certain examples, the cylindrical wall or wall sections 94 and 96 may engage with a cylindrical protrusion (not shown) provided around the port 32 on the top member 30, to help align the hub member 40 (and the cannula 44 with the exact center of the septum 90 as the cylindrical wall or wall sections 94 and 96 engage the cylindrical protrusion around the port 32.

In some examples, the cylindrical wall or wall sections 94 and 96 have a size and configured to provide a substantially close fit with the cylindrical protrusion around the port 32. Providing a close fit can advantageously assist in alignment of the cannula 44 with the port 32 (and the septum 90), and can advantageously cause any forces applied to the hub member 40, such as the hub member being bumped or the conduit 12 being pulled, will be applied at the interface of the cylindrical wall or wall sections 94 and 96 and the cylindrical protrusion around the port 32, rather than at the connection features 42*a* and 43*a*.

It is noted that the pads 48 and 49 in FIGS. 7-13 have different configurations than the pads 48 and 49 in FIGS. 1-6. However, any of those pad configurations of the various examples described herein (or other suitable pad configurations) may be employed on any particular example described herein. In the illustrated examples, the pads 48 and 49 are provided with a scalloped, contoured surface that can provide a tactile indicator, for allowing a user to feel the proper locations to apply a squeezing force. Other examples may include pad surfaces having other contours or shapes that can be readily identified, tactilely. In those or other examples, the pads 48 and 49 can include convex protrusions, concave recesses, or other shapes. Alternatively, a separate tool can also be used to grip the pads 48 and 49 and apply the squeezing force described herein.

While various exemplary embodiments have been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

We claim:

1. An infusion set device comprising:

a housing having a first surface configured to be secured to skin of a patient;

a hub member that is configured to engage and releasably attach to the housing, the hub member having:

a body having an outer perimeter and a plurality of openings through the body to enhance flexibility of the body to compress radially inward in response to a squeezing force directed radially inward relative to an axis of the hub member, each of the plurality of openings being fully within and spaced from the outer perimeter of the body;

a plurality of pads that are configured to receive the squeezing force directed radially inward relative to the axis of the hub member, wherein at least a portion of the hub member is configured to compress radially inward relative to the axis in response to the squeezing force being received by the plurality of pads;

a plurality of connection features on the portion of the hub member, the plurality of connection features being moveable from a first position radially inward relative to the axis toward a second position when the portion of the hub member is compressed radially inward, the plurality of connection features configured to engage one or more further connection features on the housing to attach the hub member to the housing when the plurality of connection features are in the first position, the plurality of connection features configured to disengage the one or more further connection features on the housing to release the hub member from being attached to the housing when the plurality of connection features are moved a definable distance toward the second position, an opening of the plurality of openings surrounds partially a section of the body, wherein the opening of the plurality of openings comprises a plurality of arcuate portions, a first straight portion, and a second straight portion that are linked, wherein the first straight portion and the second straight portion are parallel, wherein two or more of the plurality of arcuate portions are linked together by the first straight portion, wherein a connection feature of the plurality of connection features is supported by the section.

2. The infusion set device of claim 1, wherein the plurality of connection features on the hub member comprise a plurality of feet or protrusions extending radially outward relative to the axis.

3. The infusion set device of claim 1, wherein the plurality of connection features on the hub member and the one or more further connection features on the housing are configured to allow the hub member to be rotatable about the axis relative to the housing when the hub member is engaged with the housing and the plurality of connection features are moved the definable distance toward the second position, and are configured to inhibit the hub member from rotating about the axis relative to the housing when the hub member is engaged and attached with the housing and the plurality of connection features are in the first position.

4. The infusion set device of claim 1, wherein the plurality of connection features and the one or more further connection features are configured to allow the hub member to be rotatable about the axis relative to the housing when the hub member is engaged and attached with the housing and the plurality of connection features are in the first position.

5. The infusion set device of claim 1, wherein the body of the hub member has a disc-like shape that is coaxial with the axis, wherein the plurality of pads comprise a first pad and a second pad located on opposite sides of the axis, and wherein the portion of the hub member that is configured to compress radially inward comprises at least a portion of the disc-like shape made of a compressible material.

6. The infusion set device of claim 1, wherein the hub member further comprises a plurality of legs, each of the plurality of legs having at least one of the plurality of connection features, each of the plurality of legs extending outward from the body of the hub member.

7. The infusion set device of claim 6, wherein the plurality of connection features on the hub member comprise at least one foot or protrusion on each of the plurality of legs, the at least one foot or protrusion extending radially outward relative to the axis.

8. The infusion set device of claim 1, wherein the hub member further comprises a cannula member having a fluid channel and configured to extend at least partially into a connection port on the housing when the hub member is engaged with the housing.

9. The infusion set device of claim 8, wherein:

the cannula member of the hub member has a first length portion that extends from the body of the hub member and is received at least partially into the connection port of the housing when the hub member is engaged with the housing; and the cannula member of the hub member has a second length portion that flares or tapers outward to a wider outer diameter relative to the first length portion, the second length portion coupling the first length portion to the body of the hub member.

10. The infusion set device of claim 8, wherein the hub member further comprises a port for connection to a fluid flow conduit, the port being in fluid flow communication with the fluid channel of the cannula member of the hub member.

11. The infusion set device of claim 1, wherein each of the plurality of openings defines a pair of narrow sections of the body on circumferentially opposite sides of a respective one of the plurality of pads, wherein the pair of narrow sections are narrower in radial width to provide enhanced flexibility relative to other sections of the hub member.

12. The infusion set device of claim 1, wherein each of the plurality of openings defines a pair of narrow sections of the body on circumferentially opposite sides of a respective one of the plurality of pads, each of the pair of narrow sections of the body connecting a supporting section of the body to a wider section of the body, the wider section of the body being greater in radial width than each of the pair of narrow sections of the body.

13. The infusion set device of claim 1, wherein the body of the hub member has a plurality of supporting sections, wherein each of the plurality of supporting sections is radially separated from a central section of the body by a respective one of the plurality of openings, and wherein each of the plurality of connection features is supported by a respective one of the plurality of supporting sections.

14. The infusion set device of claim 1, wherein a first arcuate portion and a second arcuate portion of the plurality of arcuate portions are linked together by the first straight portion, and the first arcuate portion and a third arcuate portion of the plurality of arcuate portions are linked together by the second straight portion of the opening of the plurality of openings.

15. The infusion set device of claim 1, wherein the first straight portion and the second straight portion are orthogonal to a center axis of the body.

16. The infusion set device of claim 1, wherein a line normal to an edge of an arcuate portion of the plurality of arcuate portions at a point on the edge is parallel to an edge of the first straight portion.

17. A hub member for an infusion set device, the hub member comprising:

a body having an outer perimeter and a plurality of openings through the body to enhance flexibility of the body to compress radially inward in response to a squeezing force directed radially inward relative to an axis of the hub member, each of the plurality of openings being fully within and spaced from the outer perimeter of the body;

a plurality of pads that are configured to receive the squeezing force directed radially inward relative to the axis of the hub member, wherein at least a portion of the hub member is configured to compress radially inward relative to the axis in response to the squeezing force being received by the plurality of pads;

a plurality of connection features on the portion of the hub member, the plurality of connection features being moveable from a first position radially inward relative to the axis toward a second position when the portion of the hub member is compressed radially inward, the plurality of connection features configured to engage one or more further connection features on a housing to attach the hub member to the housing when the plurality of connection features are in the first position, the plurality of connection features configured to disengage the one or more further connection features on the housing to release the hub member from being attached to the housing when the plurality of connection features are moved a definable distance toward the second position, wherein an opening of the plurality of openings surrounds partially a section of the body, wherein the opening of the plurality of openings comprises a plurality of arcuate portions, a first straight portion, and a second straight portion that are linked, wherein the first straight portion and the second straight portion are parallel, wherein two or more of the plurality of arcuate portions are linked together by the first straight portion, wherein a connection feature of the plurality of connection features is supported by the section.

18. The hub member of claim 17, wherein the body has a disc-like shape and the axis corresponds to an axis of the disc-like shape, and wherein the plurality of pads comprise a first pad and a second pad located on opposite sides of the axis of the disc-like shape.

19. The hub member of claim 18, wherein the body further comprises a plurality of legs, each of the plurality of legs having at least one of the plurality of connection features, each of the plurality of legs extending outward from one side of the disc-like shape.

20. The hub member of claim 19, wherein the plurality of connection features comprise at least one foot or protrusion on each of the plurality of legs, the at least one foot or protrusion extending radially outward relative to the axis of the disc-like shape.

21. The hub member of claim 17, further comprising a cannula member having a fluid channel and configured to extend at least partially into a connection port on the housing when the hub member is engaged with the housing.

22. The hub member of claim 21, wherein:

the cannula member has a first length portion that extends from the body of the hub member and is configured to be received at least partially into the connection port of the housing when the hub member is engaged with the housing; and the cannula member has a second length portion that flares or tapers outward to a wider outer diameter relative to the first length portion, the second length portion coupling the first length portion to the body of the hub member.

23. A method of making a hub member for an infusion set device, the method comprising:

providing a body having an outer perimeter and a plurality of openings through the body to enhance flexibility of the body to compress radially inward in response to a squeezing force directed radially inward relative to an axis of the hub member, each of the plurality of openings being fully within and spaced from the outer perimeter of the body;

configuring a plurality of pads to receive the squeezing force directed radially inward relative to the axis of the hub member;

connecting or forming a plurality of connection features on the body, to be moveable from a first position radially inward relative to the axis toward a second position when the body is compressed radially inward;

configuring the plurality of connection features to engage one or more further connection features on a housing to attach the hub member to the housing when the plurality of connection features are in the first position, and to disengage the one or more further connection features on the housing to release the hub member from being attached to the housing when the plurality of connection features are moved a definable distance toward the second position, wherein an opening of the plurality of openings surrounds partially a section of the body, wherein the opening of the plurality of opening comprises a plurality of arcuate portions, a first straight portion, and a second straight portion that are linked, wherein the first straight portion and the second straight portion are parallel, wherein two or more of the plurality of arcuate portions are linked together by the first straight portion, wherein a connection feature of the plurality of connection features is supported by the section.

* * * * *